US011135324B2

(12) United States Patent
Rosen et al.

(10) Patent No.: US 11,135,324 B2
(45) Date of Patent: Oct. 5, 2021

(54) PORTABLE AND DISPOSABLE FAR-UVC DEVICE

(71) Applicant: Freestyle Partners, LLC, Chicago, IL (US)

(72) Inventors: Jennifer K. Rosen, Chicago, IL (US); Benjamin X. Feeney, Chicago, IL (US)

(73) Assignee: FREESTYLE PARTNERS, LLC, Detroit, MI (US)

(*) Notice: Subject to any disclaimer, the term of this patent is extended or adjusted under 35 U.S.C. 154(b) by 0 days.

(21) Appl. No.: 16/279,253

(22) Filed: Feb. 19, 2019

(65) Prior Publication Data
US 2019/0255201 A1 Aug. 22, 2019

Related U.S. Application Data

(60) Provisional application No. 62/694,482, filed on Jul. 6, 2018, provisional application No. 62/632,716, filed on Feb. 20, 2018.

(51) Int. Cl.
A61L 2/10 (2006.01)
A61L 2/00 (2006.01)

(52) U.S. Cl.
CPC ......... A61L 2/0052 (2013.01); A61L 2202/11 (2013.01); A61L 2202/14 (2013.01); A61L 2202/16 (2013.01)

(58) Field of Classification Search
CPC ...... A61L 2/0047; A61L 2/0052; A61L 2/084; A61L 2/10; A61L 2/24; A61L 9/20; A61L 2202/11; A61L 2202/14; A61L 2202/16; A61L 2209/12
See application file for complete search history.

(56) References Cited

U.S. PATENT DOCUMENTS

| 2,720,145 | A | 10/1955 | Goodfellow |
| 5,688,475 | A | 11/1997 | Duthie |
| 6,650,085 | B2 | 11/2003 | Lau et al. |
| 8,105,532 | B2 | 1/2012 | Harmon et al. |
| 8,142,715 | B2 | 3/2012 | Curry et al. |
| 8,357,914 | B1 | 1/2013 | Caldwell |
| 8,753,575 | B2 | 6/2014 | Neister |

(Continued)

FOREIGN PATENT DOCUMENTS

WO 2016196904 A1 12/2016

OTHER PUBLICATIONS

Buonanno et al. "Germicidal Efficacy and Mammalian Skin Safety of 222-nm UV Light"; Radiation Research 187, 493-501 (2017) (Year: 2017).*

Nerandzic et al., "Evaluation of a hand-held far-ultraviolet radiation device for decontamination of Clostridium difficile and other healthcare-associated pathogens" U.S. National Library of Medicine, National Institutes of Health, BMC Infect. Dis. May 16, 2012.

(Continued)

Primary Examiner — Timothy C Cleveland
(74) Attorney, Agent, or Firm — Gregory D. DeGrazia; Miller, Canfield, Paddock and Stone, PLC

(57) ABSTRACT

A handheld portable device for sanitizing a surface or air surrounding a surface. The handheld portable device includes a body that comprises a user input and a far-UVC illumination source disposed at the body. The handheld portable device also includes a power source for providing power to the far-UVC illumination source. Responsive to actuating the user input, such as by a user holding the handheld portable device, the far-UVC illumination source emits far-UVC illumination to sanitize the surface or the air surrounding the surface of pathogens.

16 Claims, 3 Drawing Sheets

(56) References Cited

U.S. PATENT DOCUMENTS

| | | |
|---|---|---|
| 8,847,174 B2 | 9/2014 | Domenig et al. |
| 9,572,903 B2 | 2/2017 | Dobrinsky et al. |
| 9,649,398 B1 | 5/2017 | York |
| 9,700,642 B2 | 7/2017 | Neister |
| 2006/0188389 A1 | 8/2006 | Levy |
| 2007/0097351 A1 | 5/2007 | York et al. |
| 2008/0295271 A1 | 12/2008 | Perunicic |
| 2008/0310996 A1 | 12/2008 | Kim et al. |
| 2011/0256019 A1 | 10/2011 | Gruen et al. |
| 2014/0063261 A1 | 3/2014 | Betensky et al. |
| 2015/0190537 A1 | 7/2015 | Kerr |
| 2016/0106873 A1 | 4/2016 | Dobrinsky et al. |
| 2017/0080251 A1 | 3/2017 | Yehezkel |
| 2017/0157276 A1 | 6/2017 | Dobrinsky et al. |
| 2017/0182305 A1 | 6/2017 | Kermode et al. |
| 2017/0216466 A1 | 8/2017 | Dujowich et al. |
| 2017/0225206 A1 | 8/2017 | Deitchman et al. |
| 2017/0245616 A1 | 8/2017 | Lakios et al. |
| 2018/0117194 A1 | 5/2018 | Dobrinksy et al. |
| 2019/0388572 A1 | 12/2019 | Cole et al. |

OTHER PUBLICATIONS

Coxworth, "Human-safe ultraviolet light used to kill airborne viruses" New Atlas article, Feb. 9, 2018, https://newatlas.com/far-uvc-airborne-viruses/53349/.

Welch et al., "Far-UVA light: A new tool to control the spread of airborne-mediated microbial diseases" Scientific Reports 8, Article No. 2752, Feb. 9, 2018, https://www.nature.com/articles/s41598-018-21058-w.

Lapook, "How ultraviolet light could be used to fight the flu" CBS news, Feb. 12, 2018, https://www.cbsnews.com/news/how-ultraviolet-light-could-be-used-to-fight-the-flu/.

International Search Report and Written Opinion dated Jun. 20, 2019 for corresponding PCT Application No. PCT/US2019/018517.

Narita, Chronic Irradiation with 222-nm UVC light induces neither DNA damage nor epidermal lesions in mouse skin, Jul. 25, 2018.

International Search Report and Written Opinion dated Mar. 23, 2021 for corresponding PCT Application No. PCT/US2020/066056.

International Search Report and Written Opinion dated Apr. 9, 2021 for corresponding PCT Application No. PCT/US2021/014386.

\* cited by examiner

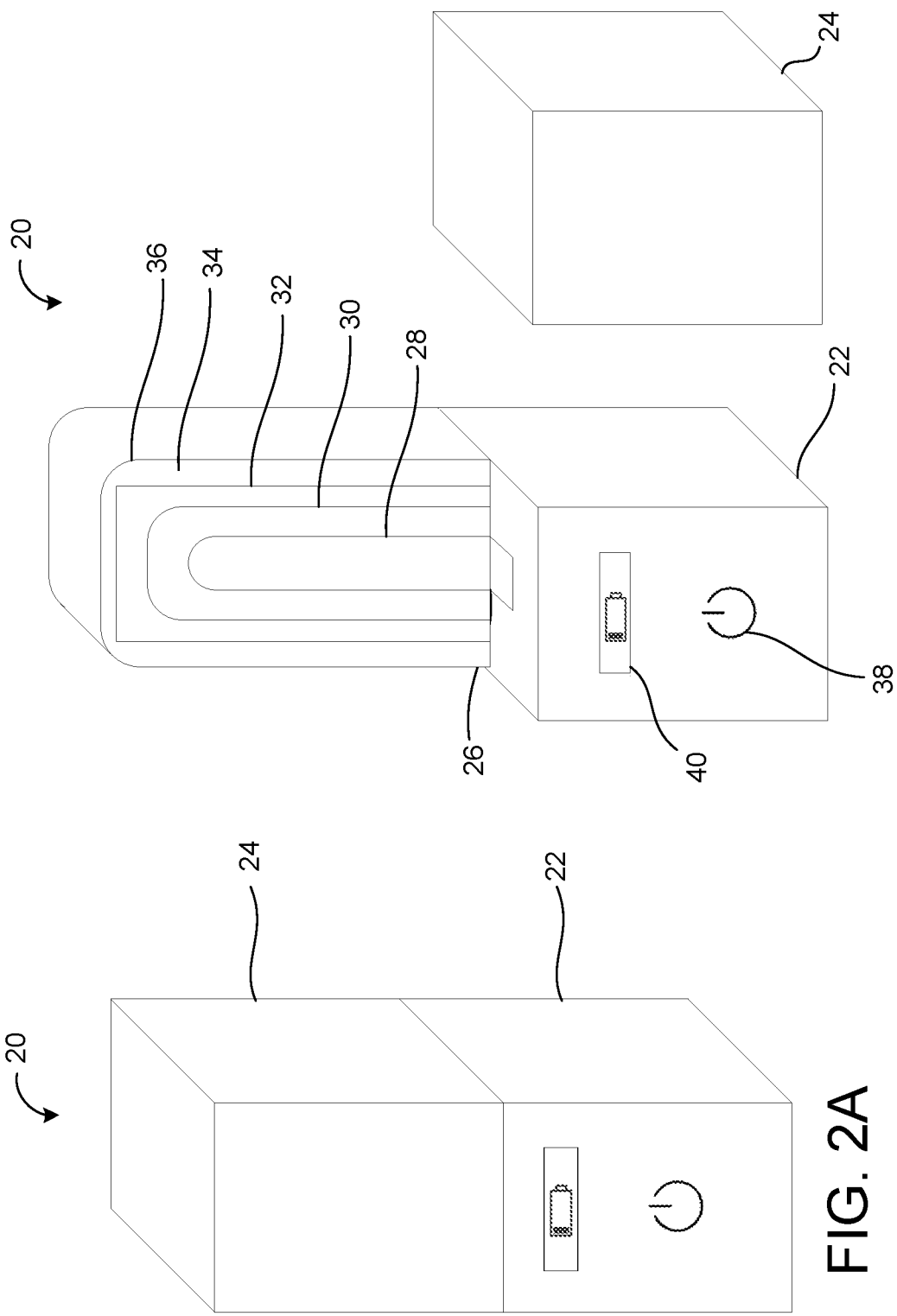

PORTABLE AND DISPOSABLE FAR-UVC DEVICE

CROSS REFERENCE TO RELATED APPLICATIONS

The present application claims the filing benefits of U.S. provisional application Ser. No. 62/694,482, filed Jul. 6, 2018, and U.S. provisional application Ser. No. 62/632,716, filed Feb. 20, 2018, which are hereby incorporated herein by reference in their entireties.

FIELD OF THE INVENTION

The present invention relates generally to light-emitting apparatus and, more particularly, to a far short-wavelength ultraviolet light emitting device.

BACKGROUND OF THE INVENTION

Pathogens such as bacteria and viruses are everywhere, such as on door handles, on phones, on television remotes, in public bathrooms, on counter tops, on the sidewalks, airborne, etc. Currently, there exists many solutions to cleaning hands from germs, such as hand sanitizer, wet wipes, etc. These products may help people who are on the go or who want a quick solution to cleaning their hands when washing with soap is not an option. However, pathogens are everywhere and it is often not feasible to put chemical wipes and/or cleaning solutions on all surfaces and/or in the air that are desired to be disinfected.

Aside from chemical wipes and other cleaning solutions, short-wavelength ultraviolet (UVC) light is a proven and effective way to kill bacteria and other pathogens. Current UVC options for killing germs/bacteria, such as portable UVC wands, stationary mechanisms to step on that help clean bottoms of shoes, phone cases, etc., are often expensive and are not readily accessible to the average consumer and/or often have a singular specific use (e.g., only cleaning the person's shoes or other element or device). Furthermore, there are risks with UVC light. For example, UVC light may cause skin cancer and/or cataracts. Therefore, a need exists for a safe for humans, handheld and/or portable and/disposable and/or rechargeable device that may be used to sanitize selected surfaces, localized areas, and/or air surrounding such surfaces to eliminate pathogens in a format that is readily available and accessible for everyday use for the average consumer.

SUMMARY OF THE INVENTION

Far-UVC light, which is a narrow spectrum within UVC light, provides the same effect of killing pathogens as UVC light, but without the harming side effects of other frequencies or wavelengths. The present invention provides far-UVC in a handheld and/or portable and/or disposable and/or rechargeable format that may be utilized in everyday, common place settings to sanitize selected surfaces, localized areas, and/or air surrounding a surface that is safe for humans while eliminating pathogens. The device may be readily available and accessible for everyday use for the average consumer.

The portable handheld device includes an illumination portion (of invisible and/or visible light) and an activation portion providing illumination in the far-UVC spectrum for generating and emitting far-UVC light on selected surfaced, localized areas and/or air surrounding a surface. The activation portion provides selective activation of the illumination portion for a duration necessary to generate and emit far-UVC light on selected surfaces, localized area and/or air surrounding a surface. The device may include a grip for gripping the device and directing the illumination in the far-UVC spectrum toward the selected surface and/or localized area thereby generating and emitting far-UVC light on selected surfaces, localized areas and/or air surrounding a surface.

In one aspect of the invention, a portable device for sanitizing a surface or air surrounding a surface includes a container or structure including an activation mechanism. At least a portion of the device or its container is transparent or translucent and, responsive to activating the activation mechanism, the portable device emits far-UVC light through the transparent or translucent portion of the device or container for a limited duration.

Implementations of the disclosure may include one or more of the following optional features. In some implementations, the device or container includes a single-use disposable device or container. The activation mechanism may include bending the device or container. Optionally, the activation mechanism includes shaking the device or container or exposing the device or container to air. In some implementations, the device or container includes a battery. The device or container may include a solar array, and the solar array is operable to charge the battery when the solar array is exposed to light (whereby the solar array, which comprises a plurality of photovoltaic cells that convert light energy to an electrical current, charges the battery). The battery, in some examples, incudes a rechargeable battery. The portable device or container may include a multi-use device. In some implementations, the activation mechanism includes a button or switch.

Another aspect of the disclosure provides a device for sanitizing a surface or air surrounding a surface. The device incudes a body that includes a user input and a far-UVC light emitting source disposed at the body. The device also includes a power source for providing power to the far-UVC light emitting source. Responsive to actuating the user input, the far-UVC light emitting source is powered and emits far-UVC light to sanitize the surface or the air surrounding the surface of pathogens.

This aspect may include one or more of the following optional features. The far-UVC light emitting source may emit far-UVC light with a wavelength between 200 nm and 230 nm. The far-UVC light emitting source comprises a filter that filters light with a wavelength of greater than 230 nm. In some examples, the device includes a visible light emitting source disposed at the body, and the visible light emitting source, when powered, emits visible light in the same direction as the far-UVC light emitting source emits far-UVC light. The emitted visible light may be emitted from the device as visible crosshairs that illuminate an area that the far-UVC light, when powered, irradiates. The visible crosshairs may be in focus when the device is an optimal distance from the surface to be sanitized, and the visible crosshairs may not be in focus when the device is not at an optimal distance from the surface to be sanitized. In some implementations, the far-UVC light emitting source emits light 360 degrees around the device.

The device may include a cell phone. The device may include a pathogen-illuminating light source that emits pathogen-illuminating light. The pathogen-illuminating light source may emit light simultaneously with the far-UVC light emitting source. The device may include a second user input, and responsive to actuating of the second user input, the pathogen-illuminating light source emits pathogen-illuminating light. The far-UVC light emitting source, in some implementations, emits far-UVC light with a wavelength of 222 nm. The device, in some examples, includes a timer. The timer indicates that a period of time has elapsed following actuation of the user input. The timer may indicate visually that the period of time has elapsed. The far-UVC light emitting source may automatically depower then the period of time has elapsed. The period of time may be selectable by a user of the device via another user input.

The device, optionally, includes a refractor. The refractor may be adjustable to adjust a width of the emitted light. The device may include a base disposed at the body, where rotating the base causes the refractor to adjust the width of emitted light. The device may include an indicator. The indicator indicates when the device is an optimal distance from the surface for sanitizing the surface. In some implementations, the indicator emits visible light when the device is an optimal distance from the surface for sanitizing the surface. The indicator may also emit an audible indication when the device is an optimal distance from the surface for sanitizing the surface.

Another aspect of the disclosure provides a handheld far-UVC device for generating and emitting far-UVC light on selected surfaces, localized areas and air surrounding a surface. The device includes an illumination portion. The illumination portion provides illumination in the far-UVC spectrum for generating and emitting far-UVC light toward a surface or space surrounding a surface. The device also includes an activation portion. The activation portion provides selective activation of the illumination portion for a time duration sufficient to episodically generate and emit far-UVC light to sanitize the surface or space. The device also includes a grip. The grip provides a gripping surface for a user to grip the device and direct the illumination portion toward the surface or space to be sanitized and to emit far-UVC illumination toward the surface or space to be sanitized.

This aspect may include one or more of the following optional features. The surface or space may include at least one of an epidermis or a non-biological surface. The illumination portion may include a lamp. The lamp generates and emits illumination having a wavelength at or below 222 nm. The illumination portion may include a lamp that generates and emits far-UVC illumination that has a wavelength exceeding 222 nm. The device also includes a filter for filtering emitted illumination with a wavelength exceeding 222 nm. The illumination portion may include at least one selected from the group consisting of: (i) an excimer lamp and (ii) a light emitting diode. The illumination portion may otherwise be any suitable light source or illumination source or lamp that is able to emit UVC and/or far-UVC illumination when energized or powered or activated.

The illumination portion may include a focus or focusing means or feature. The focusing feature optically focuses illumination on the surface or the air (or point in space not on a surface or structure). The focusing feature, in some examples, includes a lens and an illuminated indicia. The illuminated indicia provides feedback relative to a direction of the emitted far-UVC illumination. The illumination portion, in some implementations, includes a reflective surface, and the reflective surface reflects and intensifies the far-UVC illumination generated by the illumination portion toward the surface or the air or space.

Another aspect of the disclosure provides a method of sanitizing a surface. The method includes providing a handheld device that includes a first light source that emits far-UVC light and a second light source that emits visible light. The method also includes emitting, by the first light source of the handheld device, far-UVC light. The method also includes emitting, by the second source of the handheld device, visible light. The visible light provides visible indication as to the aim direction of the emitted far-UVC light. The method also includes aiming the emitted far-UVC light toward the surface to be sanitized by directing the emitted visible light at the surface to be sanitized and indicating, by the handheld device, when the handheld device is an optimal distance from a surface to be sanitized. In response to the indication that the device is an optimal distance from the surface to be sanitized, the method includes sanitizing the surface by irradiating the surface with the emitted far-UVC light. Indicating when the handheld device is an optimal distance may include focusing the emitted visible light at the surface when the handheld device is an optimal distance from the surface to be sanitized.

Another aspect of the disclosure provides a handheld device for sanitizing a surface or air surrounding a surface, and the device includes a body that includes a user input. The device also includes a far-UVC light emitting source disposed at the body, and the far-UVC light emitting source emits far-UVC light between 220 nm and 225 nm. The device also includes a visible light emitting source disposed at the body, and the visible light emitting source emits visible light in the same direction as the far-UVC light emitting source emits far-UVC light. The emitted visible light is emitted from the device as visible crosshairs that illuminate an area that the far-UVC light irradiates. The visible crosshairs are in focus when the device is an optimal distance from the surface to be sanitized, and the visible crosshairs are not in focus when the device is not at an optimal distance from the surface to be sanitized (such as too close or too far from the surface). The device also includes a power source for providing power to the far-UVC light emitting source and the visible light emitting source. Responsive to actuating the user input, the visible light emitting source and the far-UVC light emitting source are powered and the far-UVC light emitting source emits far-UVC light to sanitize the surface or the space at which the visible crosshairs are focused.

These and other objects, advantages, purposes and features of the present invention will become apparent upon review of the following specification in conjunction with the drawings.

BRIEF DESCRIPTION OF THE DRAWING

FIGS. 2A and 2B are perspective views of another portable device that emits far-UVC light when activated in accordance with the present invention;

DESCRIPTION OF THE PREFERRED EMBODIMENTS

Figure 1:
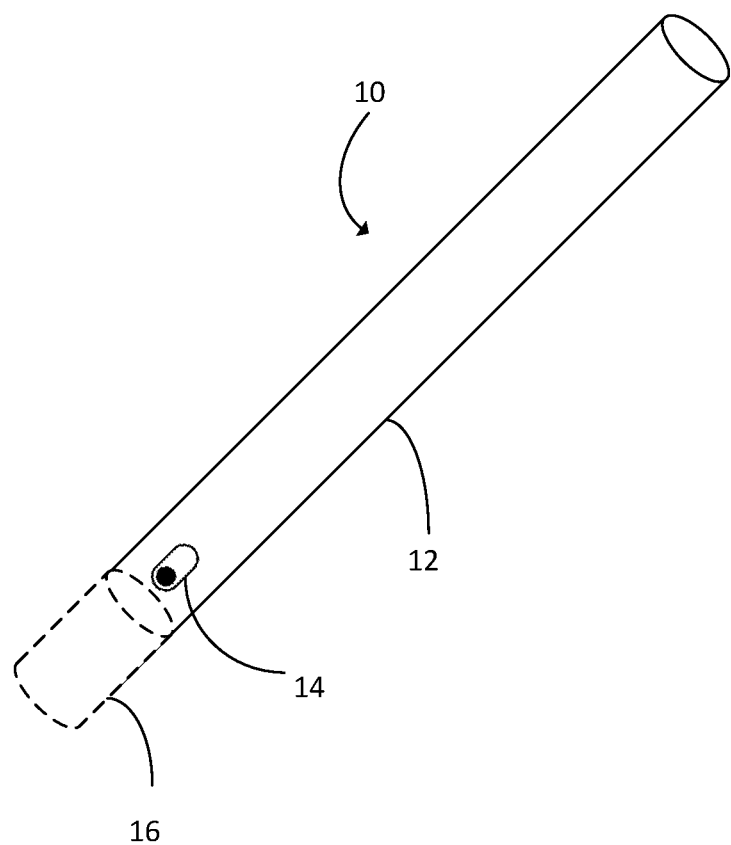
FIG. 1 is a perspective view of portable device that emits far-UVC light when activated in accordance with the present invention.

A handheld and/or portable and/or disposable and/or rechargeable device for sanitizing a surface or air surrounding the surface operates to emit far-UVC light in order to eliminate pathogens. The device includes a unit with an activation mechanism. When the activation mechanism is activated, the device emits far-UVC light. The device may then be manipulated so that the desired surface and/or air and/or space to be sanitized is irradiated in the far-UVC light, thereby cleansing the surface and/or air of pathogens.

Referring now to the drawing and the illustrative embodiment depicted therein, a device 10 includes a unit 12. The unit 12 may be any suitable shape and at least a portion of the unit 12 is transparent or translucent. The unit 12 includes an activation mechanism 14. While the illustrated embodiment shows the activation mechanism as a switch or toggle, it is understood that the activation mechanism may take any number of forms, which are described in more detail below. When the activation mechanism 14 is activated, the unit 12 emits far-UVC light through the transparent or translucent portion. Optionally, the unit includes a power source 16.

Pathogens such as bacteria and viruses are everywhere, such as on door handles, on phones, on television remotes, in public bathrooms, on counter tops, on the sidewalks, airborne, etc. Currently, there exists easy and affordable solutions to cleaning hands from germs such as Purell hand sanitizer, Wet Wipes, etc. These products help people who are on the go or who want a quick solution to cleaning their hands if washing with soap is not an option. However, pathogens are everywhere and it is often not feasible to put chemical wipes and/or cleaning solutions on all surfaces and/or in the air that are desired to be disinfected.

Aside from chemical wipes and other cleaning solutions, short-wavelength ultraviolet (UVC) light is a proven and effective way to kill bacteria and other pathogens. While currently some UVC options for killing germs/bacteria exist, such as portable UVC wands, stationary mechanisms to step on that help clean bottoms of shoes, phone cases, etc., these UVC light options are often expensive and not readily accessible to the average consumer and often have a singular specific use (e.g., only cleaning the person's shoes or other element or device). Also, there are risks with UVC light (for example, it may cause skin cancer and/or cataracts). Electromagnetic (EM) radiation includes all light or illumination that propagates electromagnetic radiant energy through space using waves. EM radiation, for example, includes both visible (to the human eye) radiation and invisible radiation, such as visible light, radio waves, microwaves, ultraviolet, gamma rays, etc. UVC light or illumination is shortwave germicidal ultraviolet EM radiation that is generally 100 nm to 280 nm in wavelength. However, far-UVC light or illumination, which is a narrow spectrum within UVC light (e.g., 200 nm to 230 nm), may provide the same effect of killing germs/bacteria without the harming side effects. As used herein, light and illumination may be used interchangeably to refer to either visible or invisible EM radiation.

In accordance with the present invention, a device to reduce germs and increase health by putting the sterilizing power of far-UVC in an inexpensive, disposable and/or single-use (or few uses), and portable format for everyday use is provided. The device comprises a small portable unit (that may take any number of shapes) that, when activated, emits far-UVC light. The unit may be activated by any number of means, such as actuating a switch or bending, pressing, squeezing, shaking and/or exposing the unit to air to activate it. After activation, the far-UVC light may be used to irradiate surfaces to kill pathogens and remains activated for a limited duration (similar to, for example, a typical chemical glow stick or chemical hand warmer). The device may sanitize many types of surfaces (e.g., an epidermis or a non-biological surface such as a table). The device may also irradiate the air to cleanse and kill pathogens above and/or around the surfaces. The device may then be easily disposed of (for example, in a trash can) once the far-UVC light terminates. The present invention is more effective and has more applications than traditional chemical wipes or cleaning solutions, is not harmful like traditional UVC light, is easy to activate, and allows for portability.

The device may utilize a variety of means to generate power to power or energize a far-UVC light source (disposed in the body or unit). For example, the device may use disposable or rechargeable batteries, chemicals, solar power, wind power, and/or any other type of mechanism to activate and/or generate the far-UVC light. Optionally, the far-UVC light source may emit light responsive to a chemical reaction when the device or unit is bent, squeezed, shaken or the like. Alternatively, the device may activate or deactivate through the actuation of a switch, button, etc.

In another aspect of the invention, the device may use a rechargeable battery to allow for multiple uses of the device (where the device may be plugged in to recharge). In yet another aspect of the invention, the device may comprise any suitable form of mobile device, such as, for example, a cell phone or other mobile device that is operable to toggle between emitting no light, regular visible light (such as a flashlight function), and far-UVC light. The device, in some examples, may include a traditional flashlight form. That is, the device may be a flashlight with a reusable UV light source (LED bulb, fluorescent bulb, excimer lamp, etc.) and a power source (replaceable batteries, rechargeable batteries, non-replaceable batteries, capacitors, etc.).

The device may emit far-UVC light in any number of ways. This includes using light bulbs of various technologies (incandescent, fluorescent, LED, excimer lamp, etc.). When including a bulb, the bulb may take any appropriate shape. For example, the bulb and/or reflector may be shaped to focus the emitted light into a relatively narrow area. The user, in some examples, may focus the emitted light (e.g., by moving a lens of the device or by actuating some other user input) between generally broad beams and generally narrow beams. The device may emit a visible indication as to the aim direction of the emitted far-UVC light. For example, the device may emit visible crosshairs (i.e., visible light in the shape of crosshairs) or other targeting indicia to assist in directing or aiming the invisible (to the human eye) far-UVC light. That is, the device may provide a method to "aim" the far-UVC light so that the intended areas are cleansed. The device may also emit visible light focused generally in the same area as the far-UVC light to assist the user in directing or aiming or guiding the far-UVC light (i.e., the user illuminates the area to be cleansed with the visible light). For example, the device may emit a beam of visible light such as a typical flashlight does, and wherever the emitted visible light irradiates a surface or space, the emitted far-UVC light also irradiates (invisibly, to the human eye) that surface or space. The visible light emitter (that emits the crosshairs) may be powered via actuation of a user input, such as the same user input that activates the far-UVC emitting light source, such that the visible light emitter and the far-UVC light emitter are operated in tandem, whereby the emitted visible light is visible at the area where the far-UVC light is directed. Optionally, the device may include a second user input, separate from the user input that activates the far-UVC emitting light source, such that the visible light emitter is operated independently of the far-UVC emitting light source. In another example, the bulb may be a lamp that emits far-UVC light in a generally 360 degree area around the bulb (e.g., a cylinder-shaped bulb). The device may then emit light in all or nearly all directions to cleanse a large area simultaneously.

In some implementations, the device may include a timer. The timer may begin measuring time when the user input to power the far-UVC light emitting light source is actuated. The timer may measure a period of time that is sufficient for the far-UVC light to eliminate a majority of pathogens (e.g., ten seconds). The timer may include a visual, audible, or tactile indication that the period of time has elapsed (e.g., an LED, an audio signal, vibration, etc.). Optionally, the timer may disable the light source at the end of the period of time. The timer may be user configurable or allow for selection among a set of predetermined time periods (e.g., ten, thirty, and sixty seconds). Thus, a user may actuate the device via a push of a button and then the device will operate for the predetermined period of time (without further input or holding of the button by the user) and then automatically shut off.

The device may include a lamps that emits far-UVC light that is generally between 180 nm and 300 nm in wavelength. For example, the lamp may emit light between 200 nm and 235 nm in wavelength. The UVC light in this spectrum is believed to kill pathogens. The device may include a filter (e.g., chemical filtration, an optical filter(s), etc.) to filter UVC light to a narrower spectrum of wavelengths (e.g., to 200 nm to 235 nm). When the light source emits a narrow spectrum of light (e.g., 200 nm to 235 nm), the filter may act as a secondary safety measure to ensure only proper wavelengths are emitted from the device. The light source may also emit a wide range of frequencies and the filter may act as the primary method of controlling wavelength. In some examples, the device may filter UVC light having wavelengths greater than 230 nm. The filter, in some implementations, has a maximum frequency response between 220 nm and 225 nm (e.g., 222 nm). UVC light with a wavelength of approximately 222 nm is still capable of destroying pathogens or otherwise providing antiseptic solutions without causing harm to the epidermis or eyesight of persons exposed to the light. Therefore, it is desirable to avoid light exceeding about 222 nm. Chemical filtration may be included in a bulb of the device or a filter located elsewhere within the device. An optical filter may be placed such that light emitted from the device passes through the optical filter. An optical filter may be included in the lamp of the device itself or as a separate element (e.g., as a film on a lens or bulb of the device or between the lens and the lamp). In some examples, the lamp 28 may only generate far-UVC light that is at or below around 222 nm so that filtration is not required.

In accordance with another aspect of the invention, the device emits light that makes bacteria and other pathogens visible to a user of the device to allow the user to determine the cleanliness of an area. For example, the device may emit a fluorescent light that illuminates bacteria. The device may emit the pathogen-illuminating light simultaneously with the far-UVC light or separately from the far-UVC light. That is, pathogens may be illuminated (i.e., made visible to the user) as the far-UVC light is in use to direct the locations to clean or, alternatively, before and after the far-UVC light is used to assist in cleaning and to assess effectiveness. The pathogen-illuminating light may be emitted from the same light source (e.g., bulb) as the far-UVC light or from a separate light source (i.e., a pathogen-illuminating light source that emits pathogen-illuminating light). The device may include an additional user input (e.g., button or switch) to activate the pathogen-illuminating light separately from the far-UVC light.

Referring now to FIGS. 2A and 2B, a far-UVC light emitting device 20 includes a base 22 and a top 24. The base 22 and top 24, while exemplified as a "lipstick case" box shape, may take any suitable form (e.g., rectangular, tubular, triangular, flexible/bendable/conformable, etc.). The top 24 attaches to the base 22 to enclose the device 20 (FIG. 2A). When the top 24 is removed (e.g., by pulling, twisting, releasing a latch, etc.), the illumination source or lamp housing 26 is exposed. Illumination, as defined herein, refers to illuminating an object or the air with visible or invisible (to a user) light. The lamp housing may include a lamp 28 or other illumination source that emits far-UVC light. The lamp 26 may be any lamp that is capable of producing wavelengths in the far-UVC spectrum (e.g., an excimer or excilamp, LED, etc.). The lamp housing 26 may also house a filter 30 that filters the wavelength of light emitted by the lamp 28. The filter 30 may be activated whenever the illumination source 28 is activated (e.g., by pushing, pressing, pulling, bending, shaking, etc. the device 20). The device may also be activated via biometrics (e.g., fingerprint sensor or face identification).

The device may also include a lens 32. The lens 32 may focus the emitted light into a narrower or broader beam. The lamp housing 26 may further include backing 34 and reflective panel 36 to further direct and control the emitted light. In some implementations, the device 20 includes an activation and/or deactivation user input 38 (e.g., a switch, slider, toggle, button, etc.). The user input 38, when actuated or activated, may power or depower the lamp 26, thereby causing the device 20 to emit far-UVC light or to stop emitting far-UVC light. The user input may episodically power the lamp 26 for a time duration sufficient to generate and emit far-UVC light to sanitize the targeted surface or space. The device 20 may further include a power level 40 that indicates the amount of power remaining in a power supply. The power supply may be a replaceable battery, a rechargeable battery, an electrical plug-in supply, a solar powered supply, etc.

Figure 4:
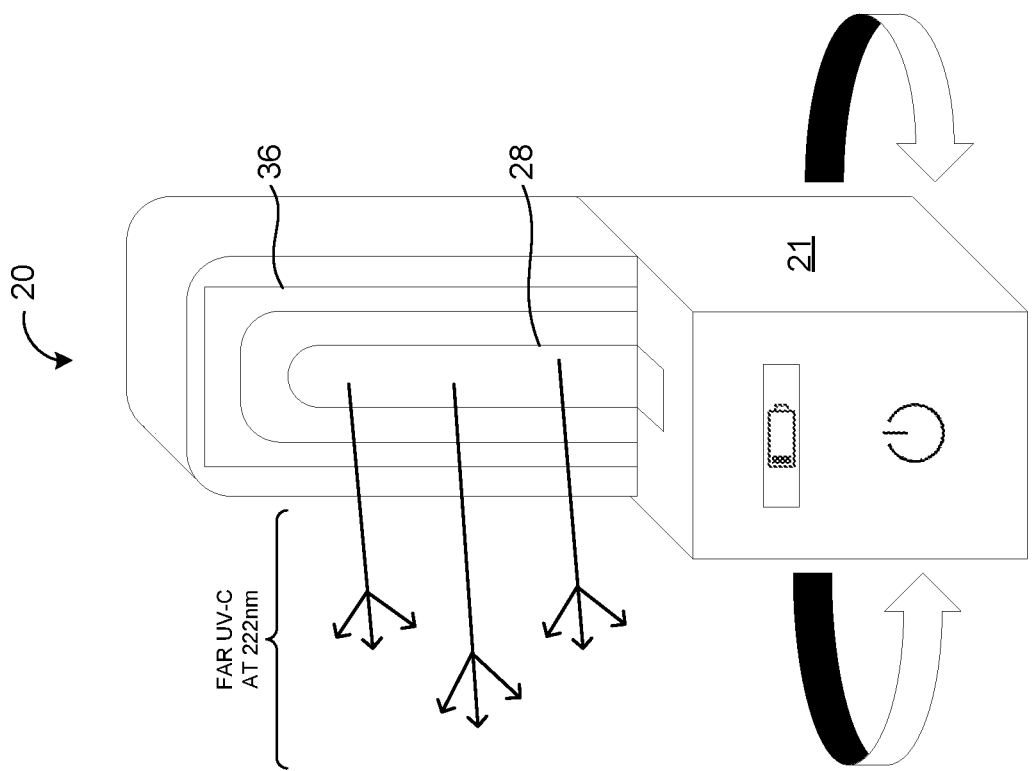
FIG. 4 is a perspective view of the portable deice of FIGS. 2A and 2B with a rotatable base to adjust a width of emitted far-UVC light in accordance with the present invention.
Figure 3:
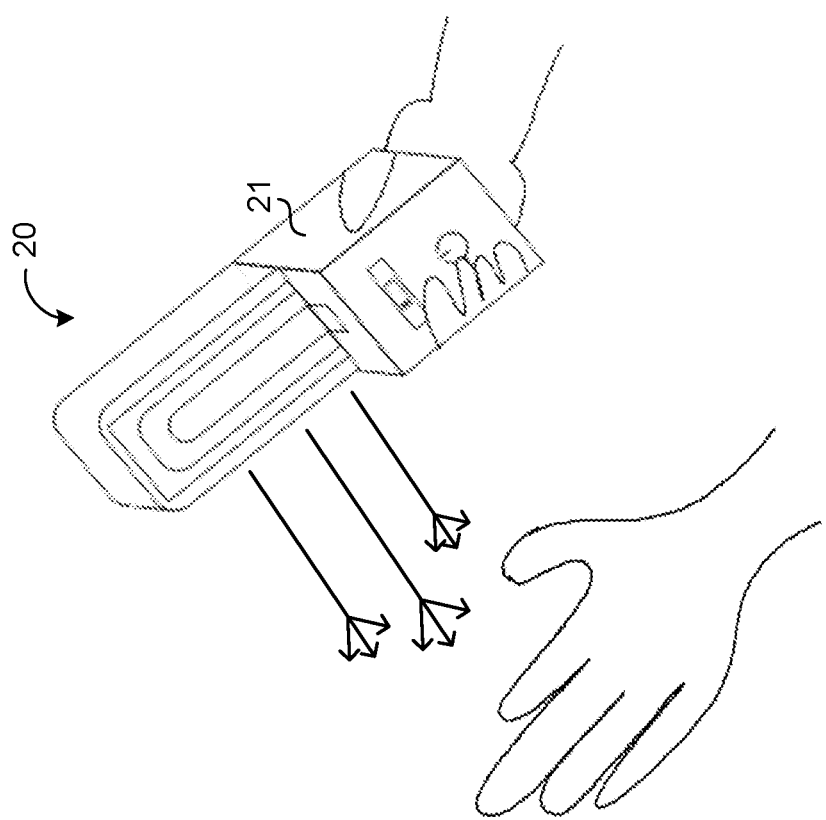
FIG. 3 is a perspective view of the portable device of FIGS. 2A and 2B emitting far-UVC light and irradiating a human hand.

Referring now to FIGS. 3 and 4, the device 20 emits far-UVC light to irradiate a target object or area to be cleansed. For example, as shown in FIG. 3, a user may hold the device 20 in one hand while irradiating his or her other hand to cleanse the hand of pathogens. The device 20 may include a grip 21 for gripping the device by the user of the device (e.g., holding the device in the user's hand). For example, the device 20 may include a rubberized surface for the user to grip while directing illumination toward the surface or air to be sanitized.

The device 20 may have an optimal operating distance. That is, the device 20 may operate most efficiently when disposed a predetermined distance from the epidermis, object or area. For example, the device 20 may preferably operate six to eighteen inches from the object or area. The optimal distance may be around twelve inches. The secondary light source 44 of the device 20 may emit a visible indicia 46 to indicate when the device is at the optimal distance from the epidermis, object or area. For example, when the secondary light source 44 of the device emits visible crosshairs, as previously discussed, the crosshairs may be fuzzy and out of focus when the device 20 is closer or further than the optimal distance, and the crosshairs may be in focus when the device 20 is at the optimal distance. The device 20 may indicate the appropriate distance in other ways (e.g., an LED on the device 20 or an audible tone). The device 20 may measure the distance via another sensor (e.g., an infrared distance sensor).

As shown in FIG. 4, the device 20 may emit far-UVC light in a narrow wavelength band (e.g., at or near 222 nm). The reflective panel 36 disposed behind the lamp 28 may increase the light density in front of the lamp 28, thereby increasing the effective distance between the device 20 and the intended target area. The device 20 may include a refractor 48 to focus the light by, for example, opening or closing an aperture or by moving or manipulating the lens or the reflective panel. The light may be focused, for example, by twisting 50 the base 22 of the device 20, much like twisting an adjustable brass hose nozzle. The light may be focused in any other suitable manner (e.g., pushing a button, sliding a slider, pushing or pulling the base, turning a knob, the lens, or the lamp, etc.). Such adjustment allows for the device 20 to irradiate a broader or narrower swath of area as desired by the user.

In accordance with the present invention, the device provides a means to sanitize small surface areas and/or the air surrounding the surface areas. For example, shoes before entering house, faucets in restroom, door handles, public table before eating, utensils, toys, remote control, sinks, office spaces, etc. When activated, the device works to eliminate harmful, illness causing bacteria and germs that are not visible to the human eye.

Changes and modifications in the specifically described embodiments can be carried out without departing from the principles of the invention, which is intended to be limited only by the scope of the appended claims, as interpreted according to the principles of patent law including the doctrine of equivalents.

The invention claimed is:

1. A handheld portable device for sanitizing a surface or air surrounding a surface, the handheld portable device comprising:
    a body that comprises a user input;
    a far-UVC illumination source disposed at the body;
    a visible illumination source disposed at the body; and
    a power source for providing power to the far-UVC illumination source;
    wherein, responsive to actuation of the user input by a user of the handheld portable device, the far-UVC illumination source and the visible illumination source are powered and the far-UVC illumination source emits far-UVC illumination to sanitize the surface and the visible illumination source emits visible indicia onto the surface that is illuminated by the far-UVC illumination source, wherein the visible indicia presents focused illumination indicative of the handheld portable device being disposed at an optimal distance from the surface to be sanitized, and wherein the visible indicia does not present focused illumination indicative of the handheld portable device being disposed at an optimal distance from the surface to be sanitized.

2. The handheld portable device of claim 1, wherein the far-UVC illumination source, when powered, emits far-UVC illumination with a wavelength between 200 nm and 230 nm.

3. The handheld portable device of claim 2, wherein the far-UVC illumination source comprises a filter that filters illumination having a wavelength of greater than 230 nm.

4. The handheld portable device of claim 1, wherein the visible indicia comprises crosshairs that illuminate an area that the far-UVC illumination, when powered, irradiates.

5. The handheld portable device of claim 1, wherein the handheld portable device comprises a cell phone.

6. The handheld portable device of claim 1, comprising a pathogen-illuminating illumination source that emits pathogen-illuminating illumination.

7. The handheld portable device of claim 6, wherein the pathogen-illuminating illumination source emits illumination simultaneously with the far-UVC illumination source.

8. The handheld portable device of claim 6, comprising a second user input, and wherein responsive to actuation of the second user input, the pathogen-illuminating illumination source emits pathogen-illuminating illumination.

9. The handheld portable device of claim 1, comprising a timer, wherein the timer indicates that a period of time has elapsed following actuation of the user input.

10. The handheld portable device of claim 9, wherein the timer indicates visually that the period of time has elapsed.

11. The handheld portable device of claim 9, wherein the far-UVC illumination source is automatically depowered when the period of time has elapsed.

12. The handheld portable device of claim 11, wherein the period of time is selectable by the user of the handheld portable device via another user input.

13. The handheld portable device of claim 1, comprising a refractor, wherein the refractor is adjustable by the user to adjust a width of emitted illumination.

14. The handheld portable device of claim 13, comprising a base disposed at the body, wherein rotating the base causes the refractor to adjust the width of emitted illumination.

15. A handheld portable device for sanitizing a surface or air surrounding a surface, the handheld portable device comprising:
    a body that comprises a user input;
    a far-UVC illumination source disposed at the body;
    a lens disposed at the body;
    a visible illumination source disposed at the body;
    a power source for providing power to the far-UVC illumination source and the visible illumination source;
    wherein the visible illumination source, when powered via actuation of the user input by a user holding the handheld portable device, emits visible illumination, and wherein the far-UVC illumination source, when powered via actuation of the user input, emits far-UVC illumination, wherein the lens focuses the far-UVC illumination emitted from the far-UVC illumination source;
    wherein the visible illumination source, when powered, emits visible illumination in the same direction as the far-UVC illumination source emits far-UVC illumination, and wherein the emitted visible illumination is emitted from the handheld portable device as visible crosshairs that illuminate an area that the far-UVC illumination irradiates;
    wherein the visible crosshairs are in focus when the handheld portable device is an optimal distance from the surface to be sanitized, and wherein the visible crosshairs are not in focus when the handheld portable device is not at an optimal distance from the surface to be sanitized; and
    wherein responsive to actuation by a user of the user input, the visible illumination source and the far-UVC illumination source are powered and the far-UVC illumination source emits far-UVC illumination to sanitize the surface or space at which the visible crosshairs are focused.

16. The handheld device of claim 15, wherein the far-UVC illumination source emits far-UVC illumination having a wavelength between 220 nm and 225 nm.

\* \* \* \* \*